United States Patent [19]

Battifora

[11] Patent Number: 5,610,022

[45] Date of Patent: Mar. 11, 1997

[54] INTERNAL CONTROL FOR IMMUNOCYTOCHEMISTRY ASSAY

[75] Inventor: Hector A. Battifora, Arcadia, Calif.

[73] Assignee: City of Hope, Duarte, Calif.

[21] Appl. No.: 73,669

[22] Filed: Jun. 8, 1993

Related U.S. Application Data

[63] Continuation-in-part of Ser. No. 789,939, Nov. 12, 1991, abandoned, and Ser. No. 700,184, May 22, 1991, abandoned, which is a continuation of Ser. No. 412,450, Sep. 26, 1989, abandoned.

[51] Int. Cl.$^6$ .......................... G01N 33/53; G01N 33/574
[52] U.S. Cl. .......................... 435/7.23; 435/7.21; 435/960; 435/967; 436/518; 436/63; 436/64
[58] Field of Search ................... 435/7.23, 7.21, 435/960, 967, 243, 260; 436/8, 15, 64, 63, 813, 501, 518, 519, 535, 240.22, 240.23; 424/3

[56] References Cited

U.S. PATENT DOCUMENTS

| | | | |
|---|---|---|---|
| 4,715,988 | 12/1987 | Colin | 436/8 |
| 5,143,714 | 9/1992 | Cosgrove et al. | 424/3 |

OTHER PUBLICATIONS

Dorland's Illustrated Medical Dictionary, 26th Edition, edited by Saunders, W.B. Saunders Co., pp. 1130–1131, 1985.
Walker, et al., The Journal of Urology, vol. 142, No. 6, pp. 1578–1583, Dec. 1989.
*Histology, Cell and Tissue Biology*, Fifth Edition, edited by L. Weiss, Elsevier Biomedical, NY, 1983, pp. 88–90 & 104–107.
Vartdal, F., et al., *J. Immunol. Methods*, 92, pp. 125–129, 1986.
Nabors, Journal of Neuroscience Methods 26:25–34 (1988).

*Primary Examiner*—Toni R. Scheiner
*Attorney, Agent, or Firm*—Rothwell, Figg, Ernst & Kurz

[57] ABSTRACT

An internal control or standard is provided for the direct quantitative assay by immunocytochemistry of target molecules in tissue specimens and the like. The control may be subjected to the same conditions including immunostaining as the tissue specimen. Immunoreactivity of the control and the specimen before and after processing is compared by physical measurement, e.g., optical density as determined by a cell analysis computer system. The immunoreactivity difference of the control provides a quantative standard useful to determine the effect of the processing on the immunoreactivity of the specimen.

8 Claims, 20 Drawing Sheets

FIG.7A1

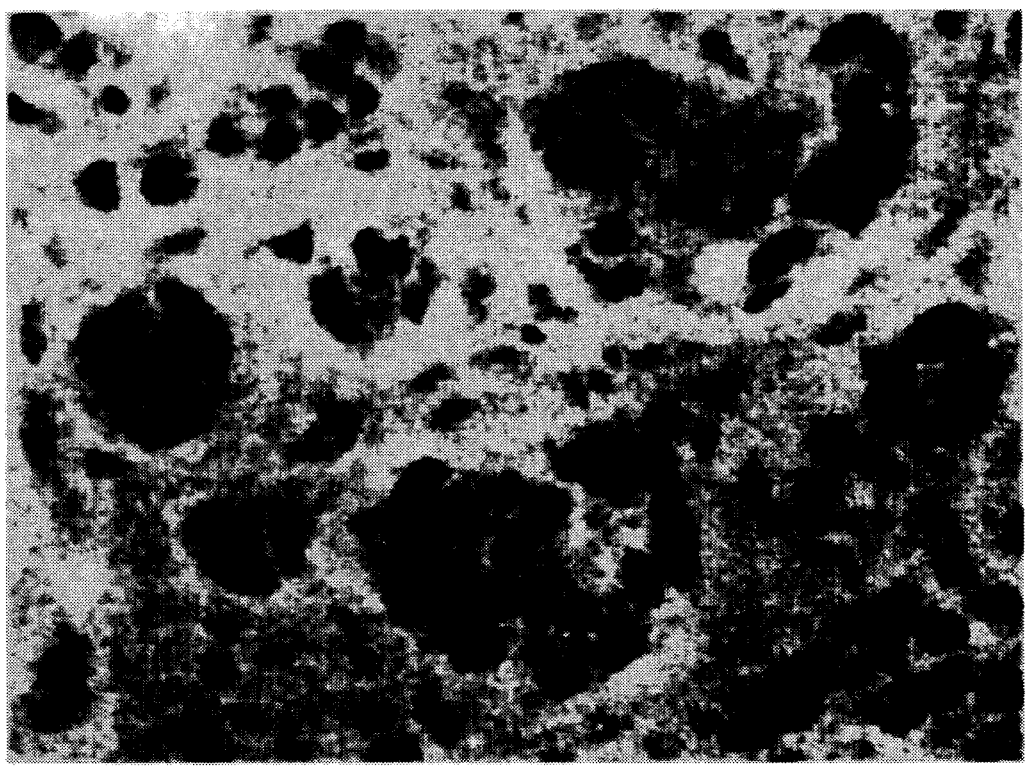
FIG.7A2

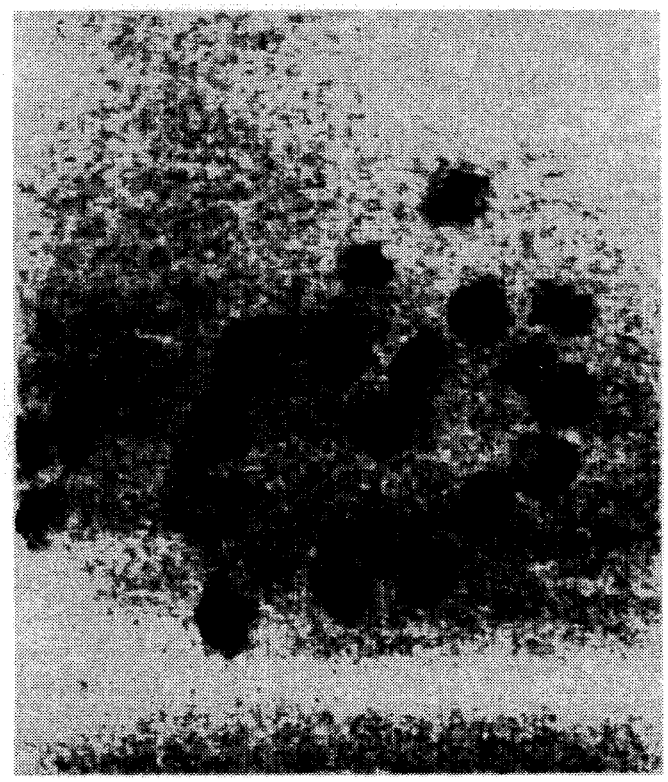
FIG.7A3

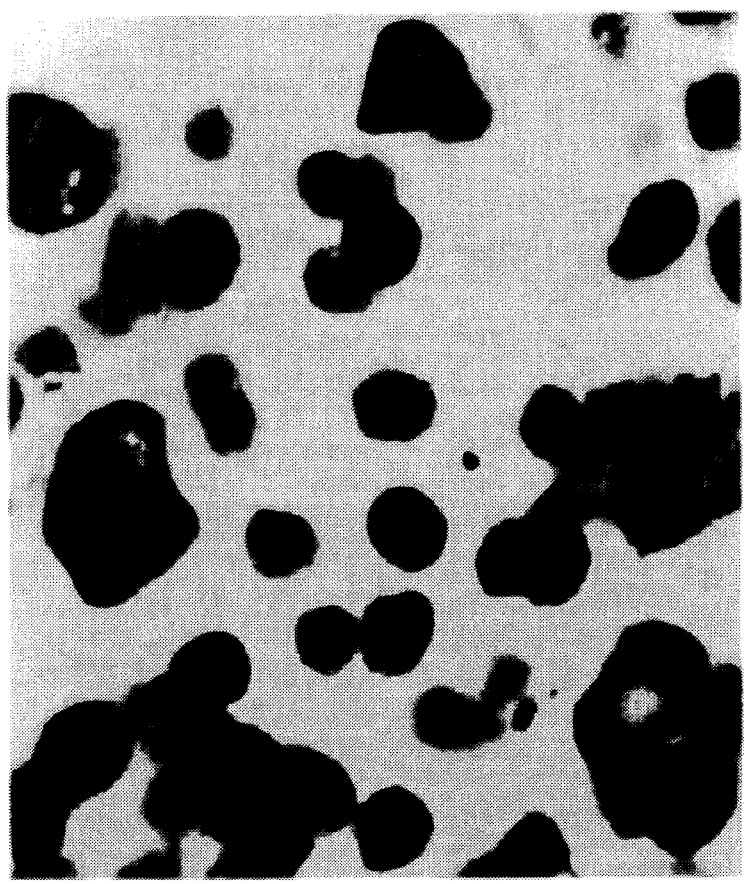
FIG.7B1

FIG.7B2

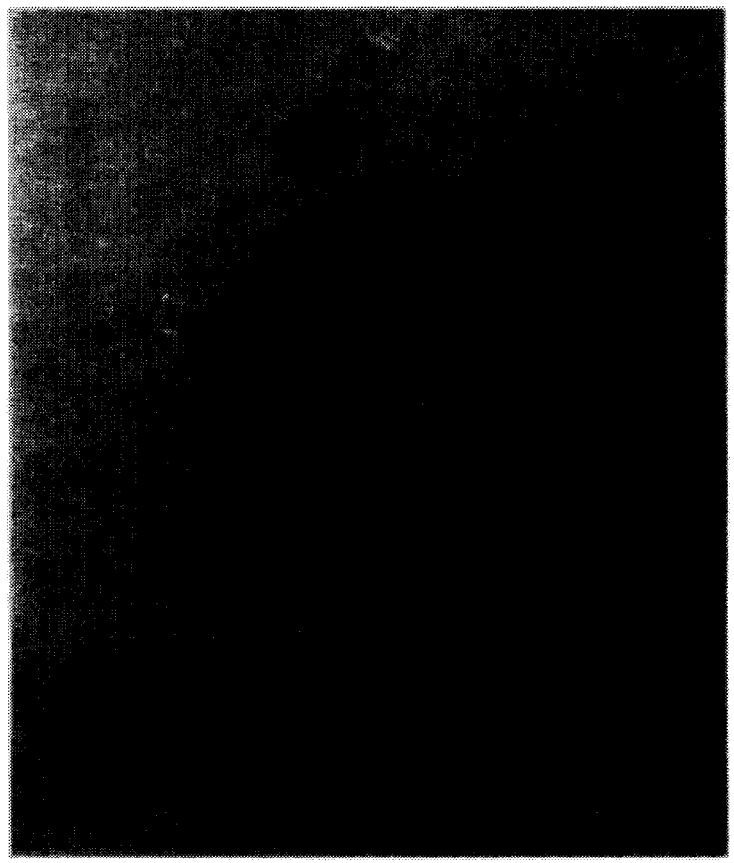
FIG.7B3

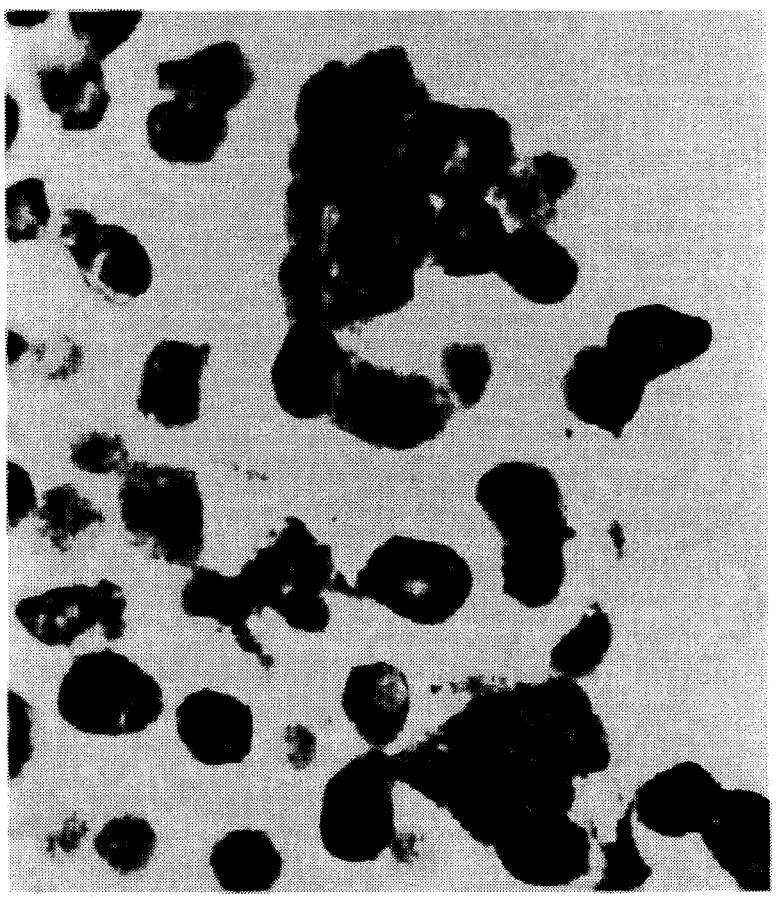
FIG.7C1

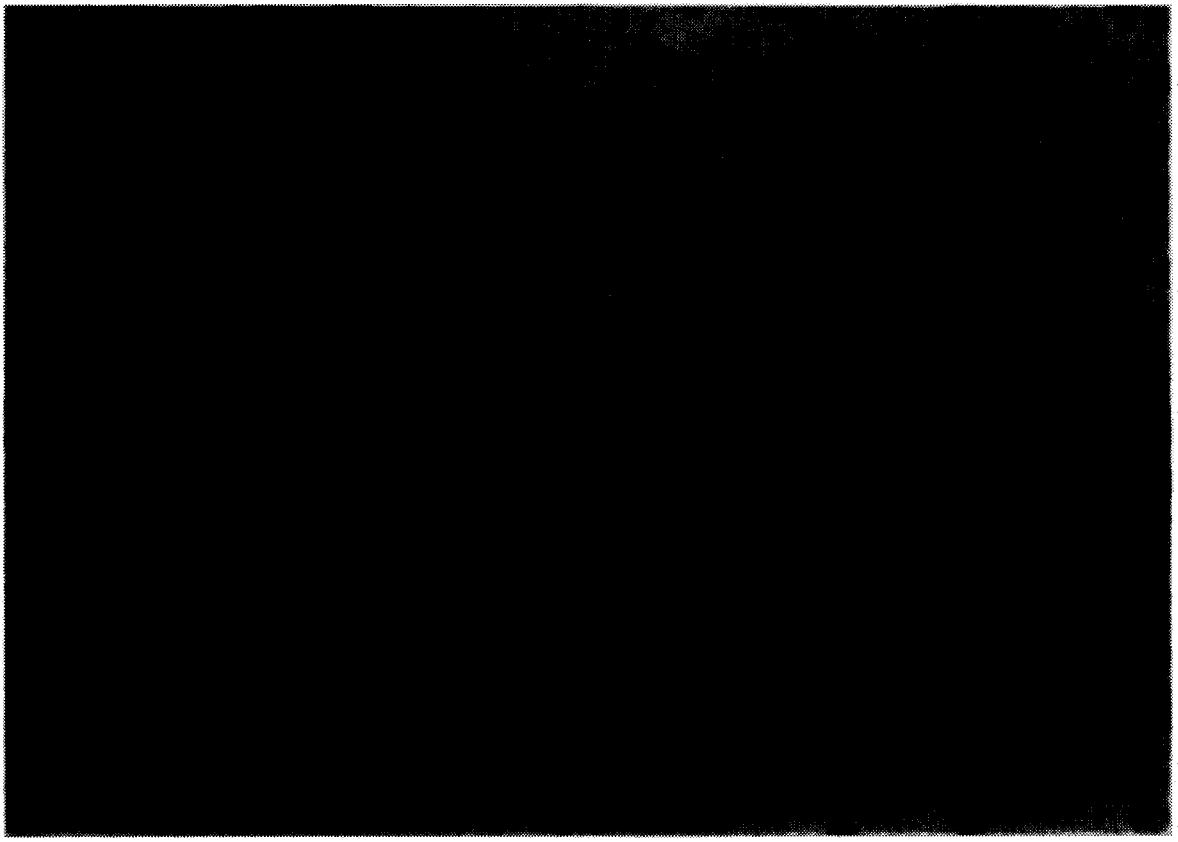
FIG.7C2

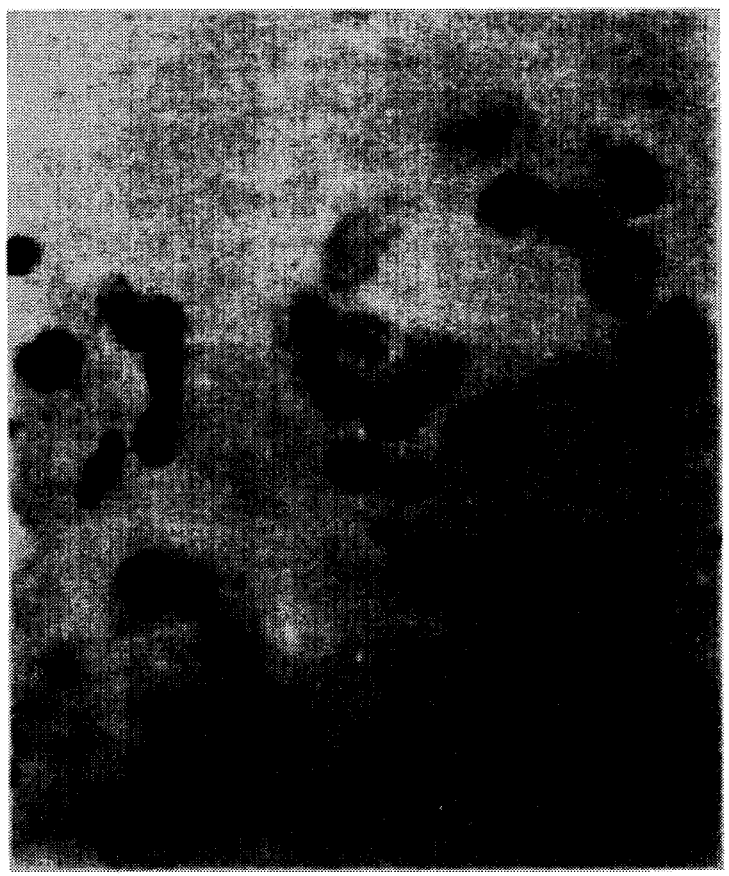
FIG. 7C3

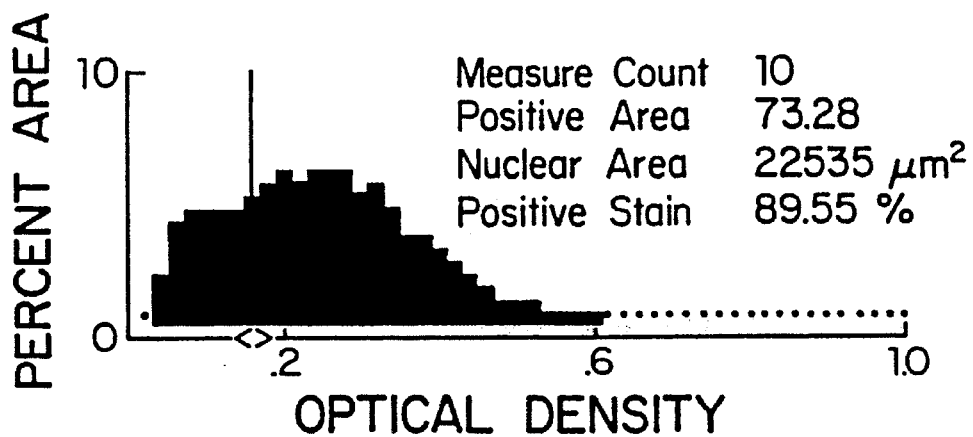
Quicgel, 12 hrs.
FIG. 8A1
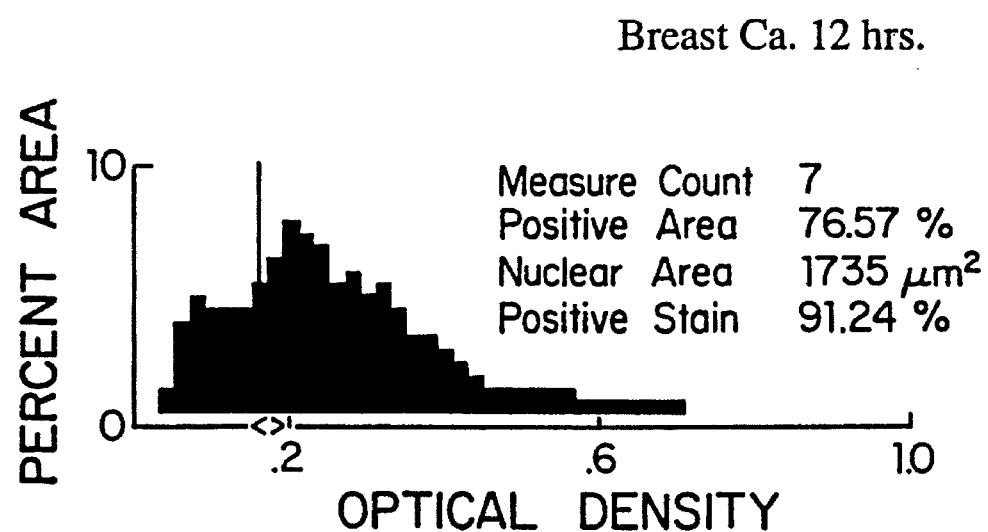
FIG. 8A2

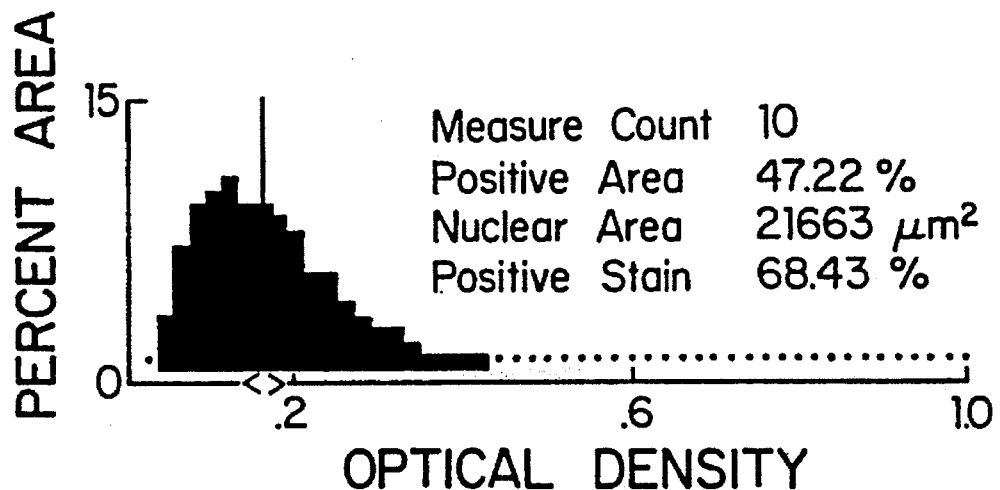
Quicgel, 24 hrs.
FIG. 8B1
Breast Ca. 24 hrs
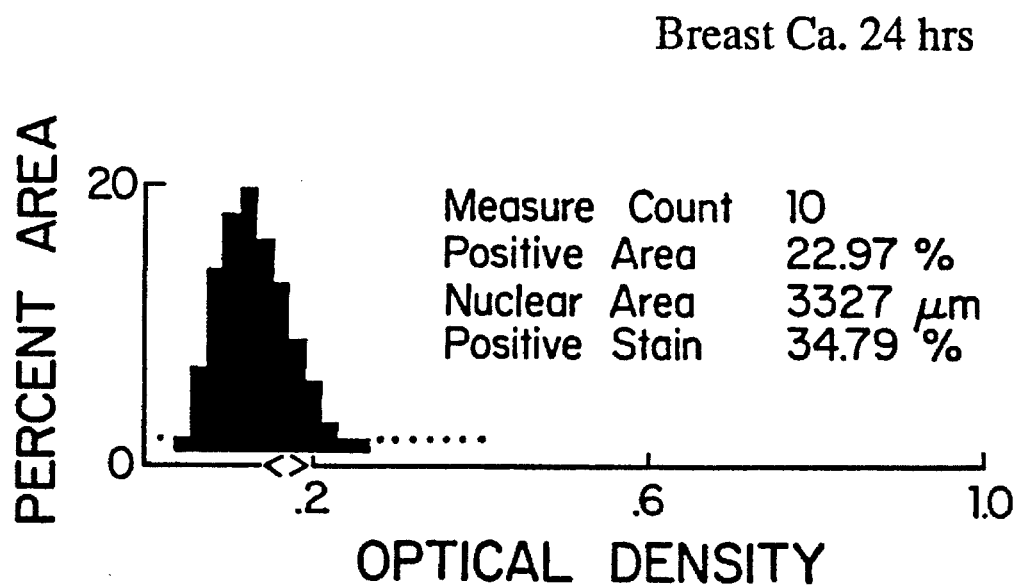
FIG. 8B2

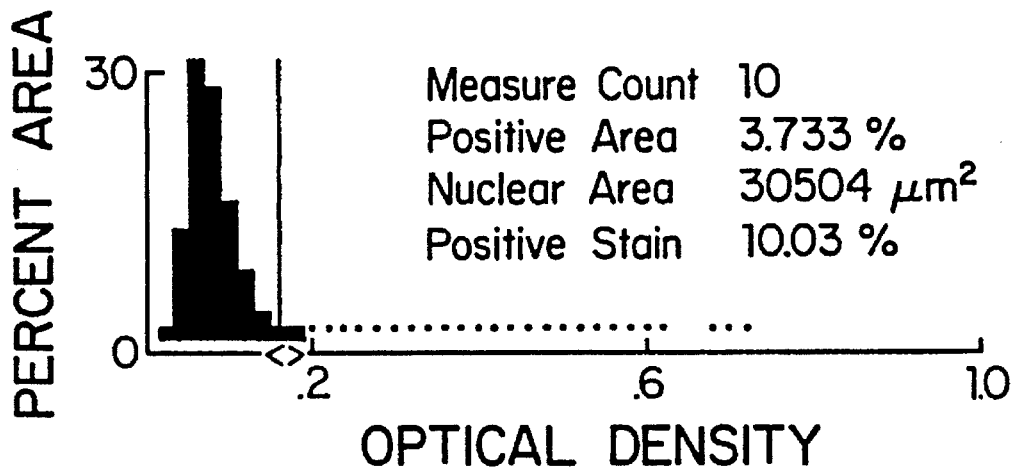
Quicgel, 72 hrs.
FIG. 8C1
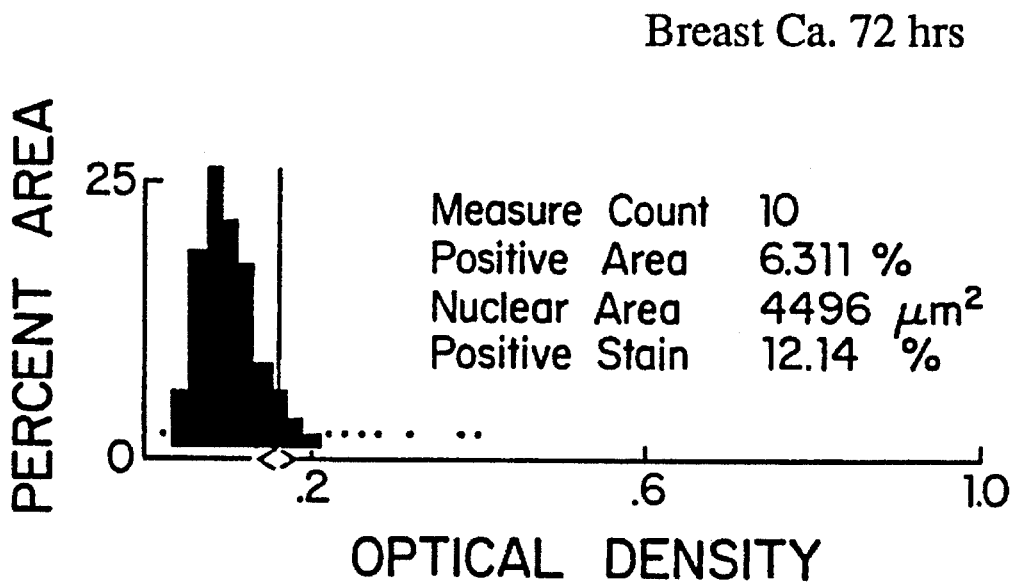
FIG. 8C2

INTERNAL CONTROL FOR IMMUNOCYTOCHEMISTRY ASSAY

This invention was made with government support under Grant No. RO1CA37194 awarded by the National Institutes of Health. The government has certain rights in the invention.

This application is a continuation-in-part of each of application Ser. Nos. 07/700,184 filed May 22, 1991, now abandoned, and 07/789,939 filed Nov. 12, 1991, now abandoned. Application Ser. No. 07/700,184 is a continuation of Ser. No. 07/412,450 filed Sep. 26, 1989, now abandoned.

TECHNICAL FIELD

This invention provides an internal control which permits quantitative immunohistochemical assays (IHC) notwithstanding the variable and unpredictable antigen loss consequent from tissue processing.

BACKGROUND OF THE INVENTION

Biochemical assays are routinely used to quantify target molecules in tissue specimen homogenates. Such assays are based on variations in the numbers of normal cells and abnormal cells which express target molecules. IHC assays, in contrast, entail a direct measurement made only on abnormal target molecule expressing cells.

IHC is ideally suited for large sale retrospective studies based on archival material. It provides information not easily obtained by extractive methods of analysis such as the subcellular location of an antigen, heterogeneity of its distribution and correlation with important morphologic parameters. Heretofore, several obstacles have impeded full realization of the advantages theoretically offered by IHC.

IHC quantitation based on paraffin embedded material is difficult, if not impossible. For several reasons, IHC methodology based on visual estimation of the intensity of the immunostaining reaction does not provide a precise, reproducible quantitative assay. Among others, (i) the various tissue processing steps (fixation time, type of fixative, dehydration, embedding and related procedures) each cause some variation, in particular loss of antigen, which modifies the immunostain signal; (ii) immunostain signal strength is a function of tissue section thickness and of staining procedure variables, such as antibody concentration, timing, and chromogen type.

SUMMARY OF THE INVENTION

Pursuant to this invention, a gel such as agar or gelatin containing a suspended cell line expressing a known amount of a target molecule is prepared. The gel may be sliced, frozen, or freeze dried. Slices or sections of the gel provide pseudo tissues for use as internal controls in IHC assays.

In the IHC assays of the invention, a pseudo tissue is placed within a tissue cassette alongside the tissue specimen to be assayed. The pseudo tissue and the tissue specimen are concurrently fixed and processed through staining. An appropriate physical measurement of immunoreactivity such as optical density is made on the pseudo tissue and the tissue specimen before and after processing.

The immunoreactivity difference in the pseudo tissue before and after processing provides a standard for determining the effect of the processing steps on the immunoreactivity of the tissue specimen. From this standard, the pre-processing immunoreactivity of the tissue specimen may be determined.

An important embodiment of the invention comprises layered gel sections or pseudo tissues, thus providing two or more cell lines expressing dissimilar known amounts of one antigen or known amounts of each of several different antigens.

DESCRIPTION OF THE FIGURES

FIGS. 7A1, 7A2, 7A3, 7B1, 7B2, 7B3, 7C1, 7C2 and 7C3 illustrate a comparison of staining for estrogen receptor in one of the breast cancer specimens of FIG. 6 and its corresponding gel at various intervals of tissue fixation. Vimentin staining of the gel per se is also shown. Gradual reduction of the intensity of the nuclear staining in the specimen as well as the gel is apparent.

FIGS. 8A1, 8A2, 8B1, 8B2, 8C1 and 8C2 are computer assisted plots of optical density of the estrogen receptor stains of the breast cancer specimens of FIG. 6 and their respective gel controls. The parallel relationship of the reduction of immunostaining between sample and control is evident from the similarity of the resulting plot.

DETAILED DESCRIPTION OF THE INVENTION

The variable, and often unpredictable effect of fixation and processing on the preservation of tissue antigens is in great part responsible for poor reproducibility of immunohistochemical assays among, and even within, laboratories. Reliable quantitative immunohistochemical analysis based on paraffin-embedded tissues is not possible unless these impediments are eliminated.

Figure 9:
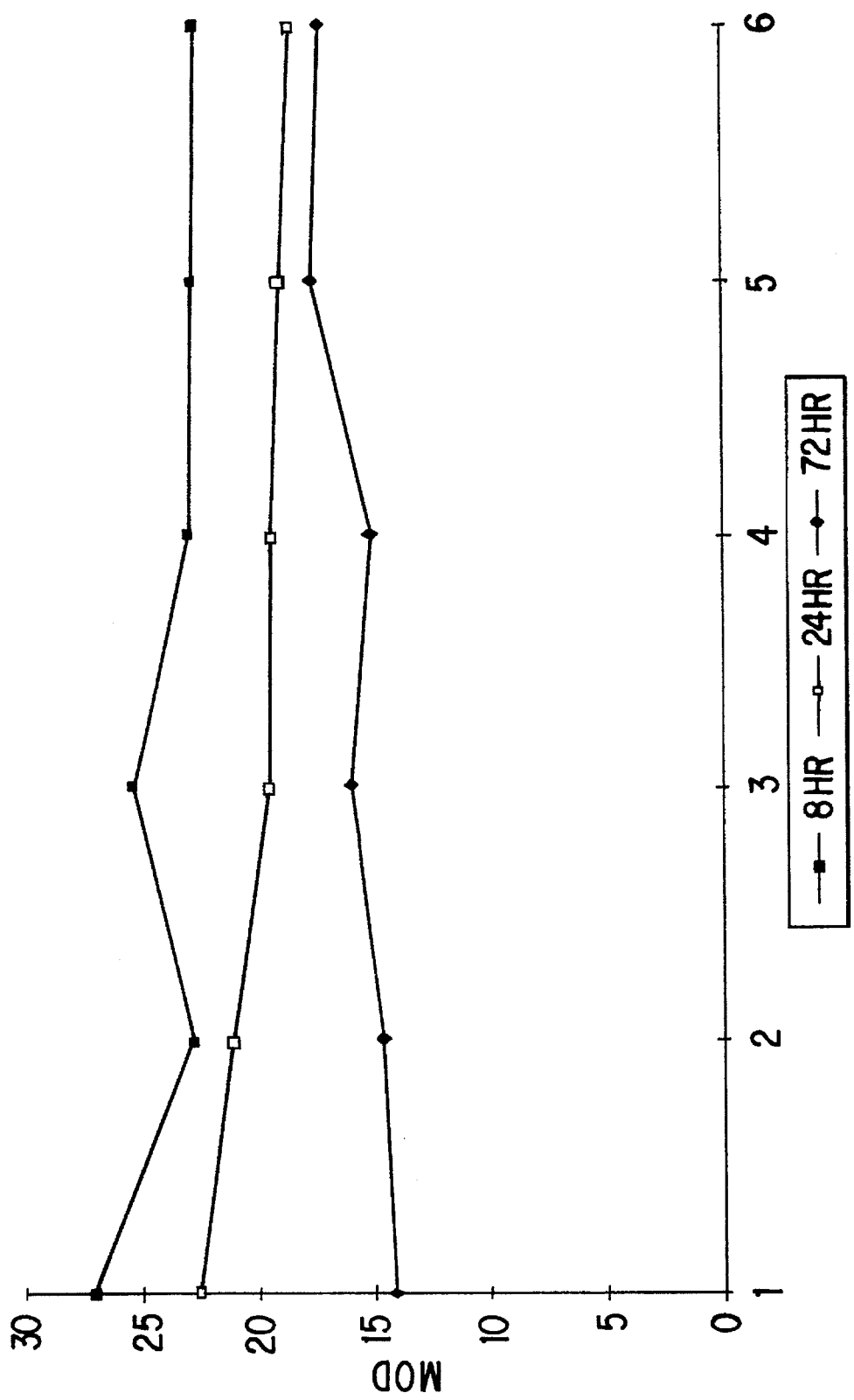
FIG. 9 includes curves which show mean optical density of MCF-7 cells in gels fixed for 8, 24 and 72 hours. A total of 18 separate gels were prepared and analyzed. As the Figure shows, the longer the fixation time, the lower the median optical density (MOD).

Vimentin is routinely used as a built-in control molecule to gauge the status of antigen preservation in immunohistologic preparations. Vimentin immunostains provide information on the adequacy of fixation and aid in the selection of fields for the interpretation of results obtained with other immunostains (FIG. 9). However, assessment of antigen preservation based on a surrogate molecule such as vimentin has the limitation that not every antigen is affected equally by tissue fixation and processing.

This invention provides a quantitative immunohistochemical assay for a target molecule which comprises (i) concurrently fixing, processing and embedding a section of an agar or gelatin gel containing cells expressing a known amount of a target molecule and a tissue specimen to be assayed for expression of said target molecule, (ii) quantitatively determining the target molecule content of the tissue specimen after fixing, processing and embedding and the difference in the target molecule content of said section of said gel before and after fixing, processing and embedding, and (iii) utilizing the difference in the target molecule content of said section as determined in step (ii) as a standard for determination of the target molecule content of said tissue specimen before processing.

The pseudo tissue provides total internal control from fixation to immunostaining. Differences due to variation in section thickness or in the sensitivity of the immunostaining procedure are eliminated.

The invention is not limited to the exemplified embodiments which illustrate its application to quantitative immunohistochemistry of hormone receptors in paraffin-embedded tissues. It also encompasses application of the same technology to any desired molecules simply by selection of appropriate cell lines from a plethora of available types.

Choice of cell line type depends upon the type of antigen or other molecules to be measured. Preferably the pseudo tissues which include cells transfected with a gene coding for the desired molecule or antigen are used. Target molecules or antigens which may be quantified in a specimen by use of this invention include, for example, proteins expressed by oncogenes, cell growth factors, receptor molecules and any of the various molecules that control cell proliferation.

Prior to use in an IHC assay, the pseudo tissues of this invention are fixed, preferably in paraformaldehyde, for not more than ten minutes. It has been repeatedly observed that such brief fixing does not significantly affect the staining reaction.

In the preferred practice of the invention, the cell lines which express target molecules are suspended in a known, predetermined amount of an aqueous solution containing from about 2% to 3% by weight of agar, gelatin, or similar gel forming material. The gel formed upon solidification of such a suspension is sliced to provide sections or pseudo tissues preferably from about 2 mm to about 3 mm in thickness. In multilayer embodiments of the invention, boundaries between the gel layers are marked by india ink or a similar marker.

Figure 1:
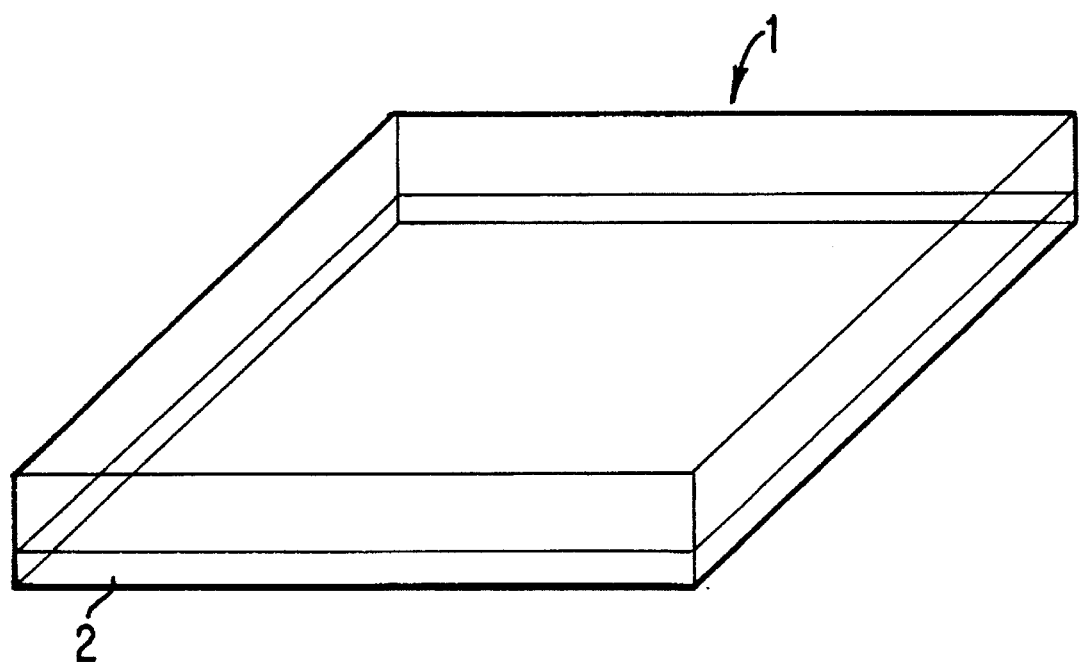
FIG. 1 depicts a mold 1 containing a first gel layer 2. A cell line expressing a known amount of a target molecule (not shown) is suspended in the gel layer 2.

In the embodiment of the invention, shown by FIG. 1, a known, predetermined quantity of the cells or antigens is suspended in an embedding medium such as agar or gelatin. A first layer is then cast in a mold. A portion or section of the single gel layer so produced can be used directly as an internal standard or pseudo tissue.

Figure 2:
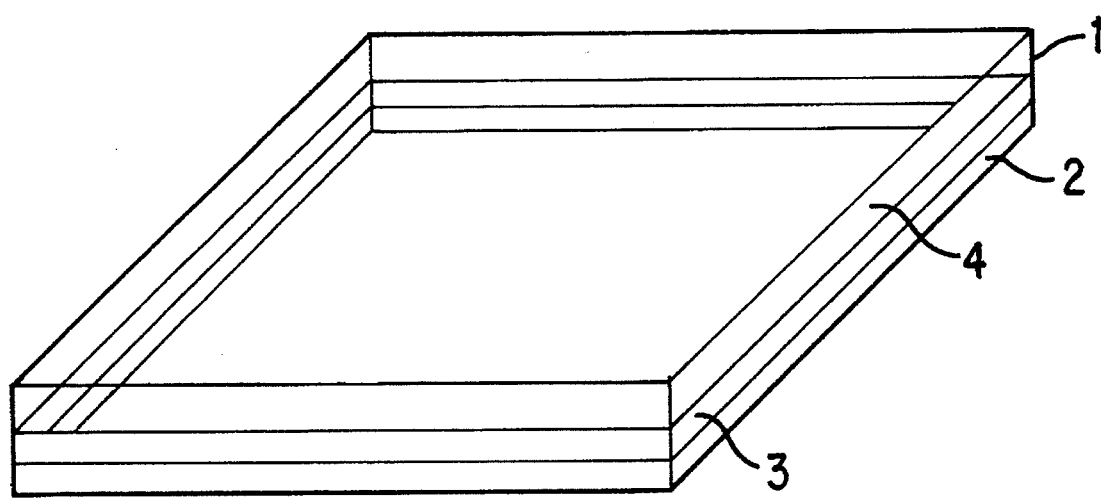
FIG. 2 depicts a mold 1 containing a first gel layer 2 which includes a cell line expressing a known amount of an antigen. A second gel layer 3 includes a cell line expressing a different known amount of the same antigen expressed by the cell line in the first gel layer 2 or a cell line which expresses a known amount of a different antigen. A third layer 4 includes a cell line expressing a known amount of the same antigen or of an antigen different from that expressed by the cell lines in gel layers 2 and 3. Any desired number of such layers may be included in the layered gel embodiments of this invention.
Figure 3:
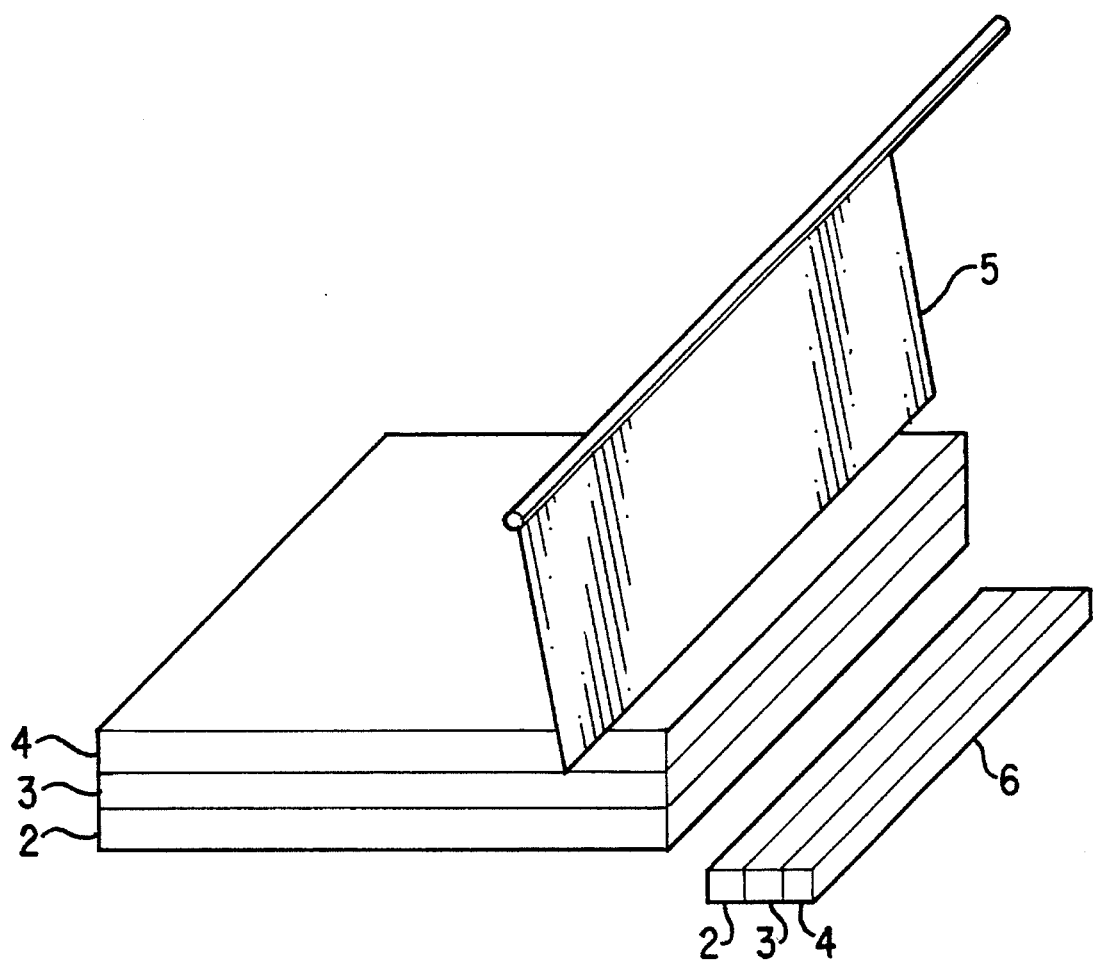
FIG. 3 illustrates the slicing of a three layered gel. First, second and third gel layers 2, 3 and 4 are sliced with blade 5 to produce internal control 6.
Figure 4:
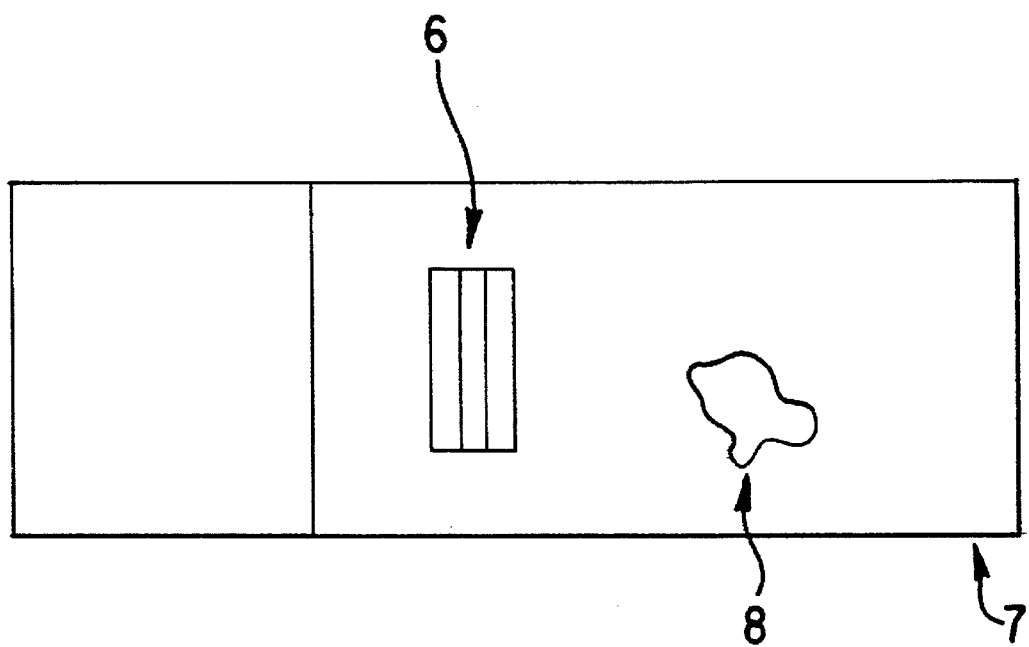
FIG. 4 illustrates a histological slide 7 with internal control 6, and assay sample 8.

Another embodiment of the invention includes multilayered internal standards, as illustrated by FIGS. 2 and 3, each layer of which contains a cell line expressing different amounts of a known antigen or known amounts of different antigens.

Figure 5:
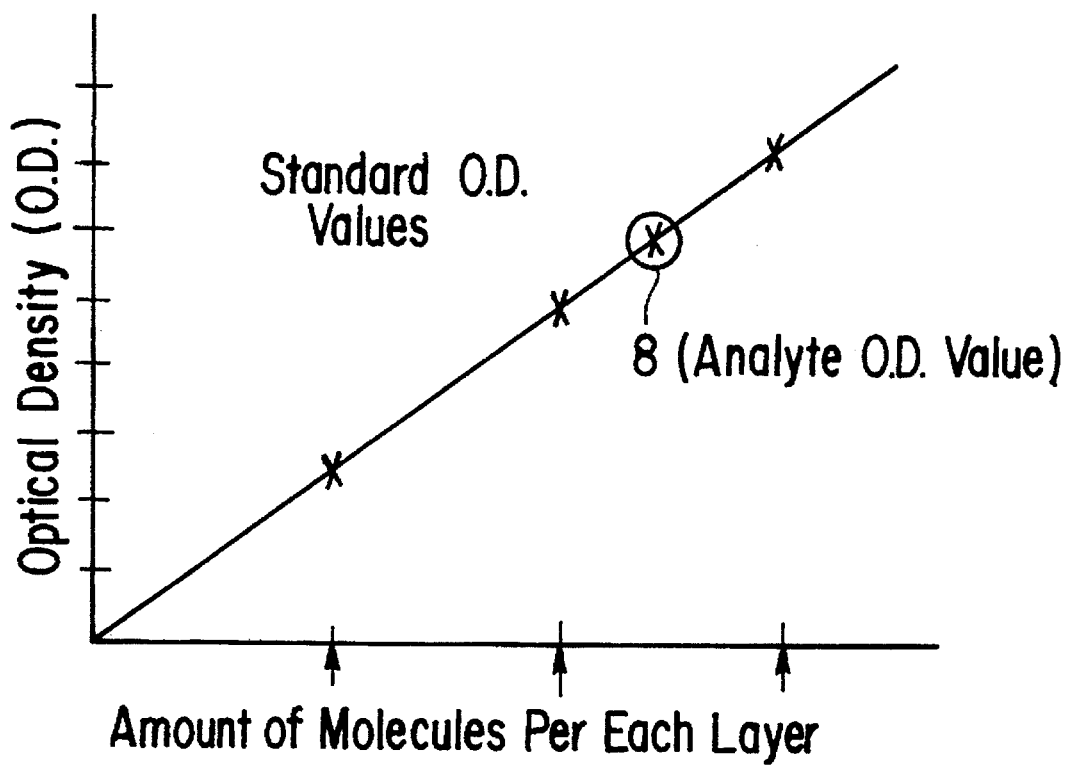
FIG. 5 is a curve illustrating one way in which the pseudo tissue internal controls of this invention may be utilized.

Optical density may be determined, e.g., with a CAS 200 image analyzer (Cell Analysis Systems, Inc., Lombard, Ill.) initially and after processing for each cell line layer of the internal standard. The data is plotted, preferably on semi-log paper to provide a standard curve against which the optical density of the tissue samples is measured. The quantity of the analyte molecule expressed by the tissue sample is determined from the curve. See FIG. 5.

This invention therefore provides, for the first time, an internal control in the form of a pseudo tissue which permits quantitative IHC assays on fixed, paraffin-embedded tissue samples.

EXAMPLE I

MCF7 (ATCC Accession No. ATB-22) and BT474 (ATCC Accession No. HTB-20) cells known to express a defined amount of the antigens (estrogen receptors and progesterone receptors) to be measured were grown in tissue culture. The cells were fixed for less than ten minutes in paraformaldehyde and suspended in a 3% agar solution (Difco, Detroit, Mich.) at 56° C. which was allowed to gel. Uniform slices, 3 mm thick, were fixed in formaldehyde for periods of time ranging from 4 to 72 hours and processed together into a single paraffin block. The cross-sectional dimensions of the block were about 2 by about 2.5 cm. Sections cut at 5 microns were immunostained for estrogen receptor (ER-ICA, Abbott, Ill.) and cERB-b2 oncoprotein (Triton Bios., Alameda, Calif.). The intensity of the immunoreactivity was measured for each time period with a CAS 200 image analyzer. Progressive reduction in the intensity of the immunoreactivity, which correlated with the lengthening of the fixation time was detected with both antigens. Significantly, such reduction was not noticeable by conventional microscopy in the ER-ICA stains.

EXAMPLE II

The most common cause of variation of immunohistochemical assays is the length of fixation in formalin. To determine the reproducibility of assay data obtained by use of the pseudo tissue controls of this invention, eighteen equal sized fragments of gels containing cultured cells from a breast cancer cell line (MCF7) were fixed in neutral buffered formalin (NBF) for 8, 24 and 72 hours, in separate tissue cassettes. The gels were then processed by standard methods to embedding in paraffin, sectioned and stained for estrogen receptor (ER) with a monoclonal antibody (H222; Abbott's Lab. North Chicago, Ill.) using a standard immunoperoxidase method. This stain produces brown nuclear staining in cells expressing ER. The intensity of the staining is directly proportional to the amount of ER being expressed by the cells. The resulting slides were examined under a cell analysis system (CAS) to measure optical density of individual nuclei. Measurements of a minimum of 100 cells per gel were taken. The results depicted by FIG. 9 are expressed in median optical density (MOD).

The MOD varied from a low of 14 to a high value of 27. The highest values always corresponded to the gels with the lower fixation time. The lowest values corresponded to the longest fixation time. Intermediate values were obtained in gels fixed for 24 hours.

It is evident from these data that the length of exposure to the fixative introduced a significant source of variation in the intensity of staining, and therefore in the MOD of the gels. Because it is known that all the gels were prepared from a single batch of MCF7 cells and therefore started with the same amount of estrogen receptors, the observed differences can only be attributed to damage to the antigen by the fixative. Thus, regardless of the MOD for each fixation time, the comparative reading of a specimen sample run in parallel with the gel should be expected to behave similarly. Compensation for the obtained OD for the tissue sample, by extrapolation from the observed OD of the gel is also possible.

This experiment also demonstrates the reproducibility of the method as only moderate variations in OD were found among the separately processed several gel samples.

EXAMPLE III

Figure 6:
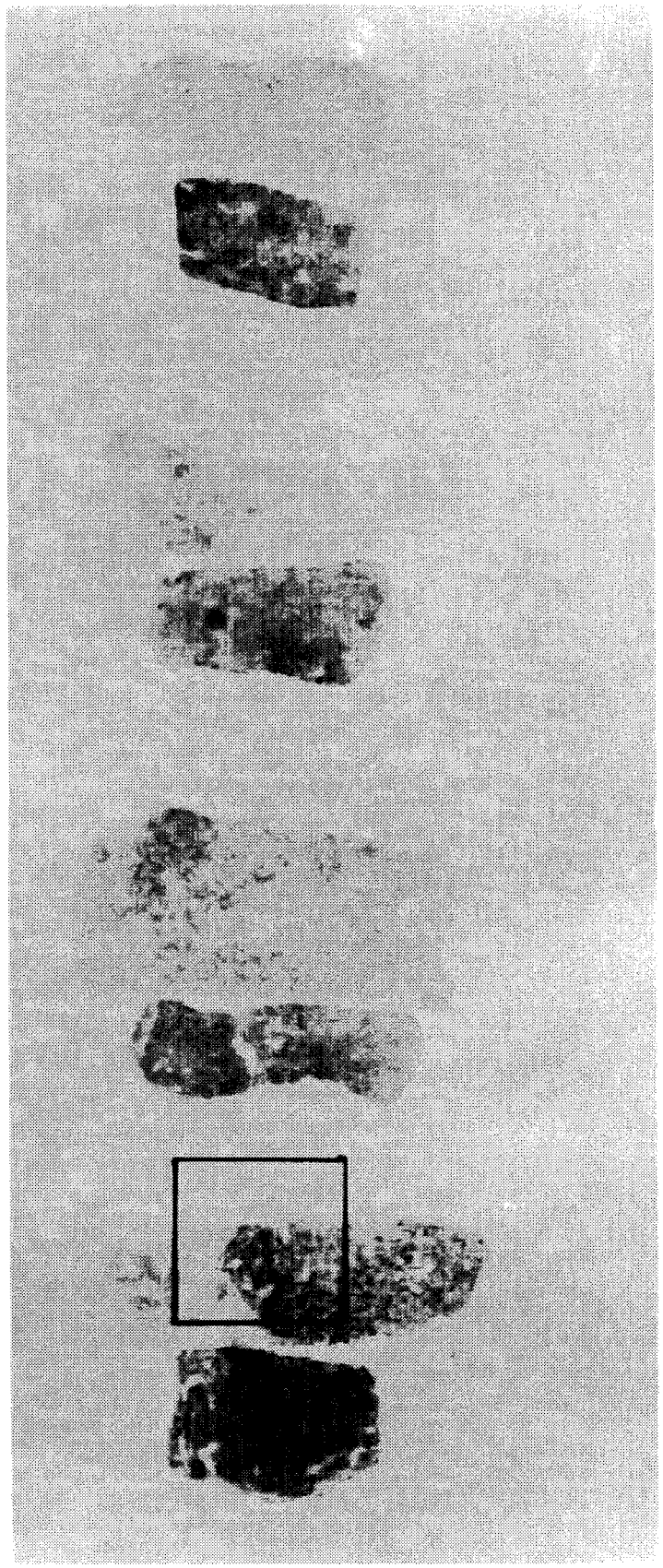
FIG. 6 illustrates the testing of one embodiment of the invention. Sections of a single block containing two (2) breast cancer specimens were fixed in formaldehyde for various periods of time.
Figure 6A:
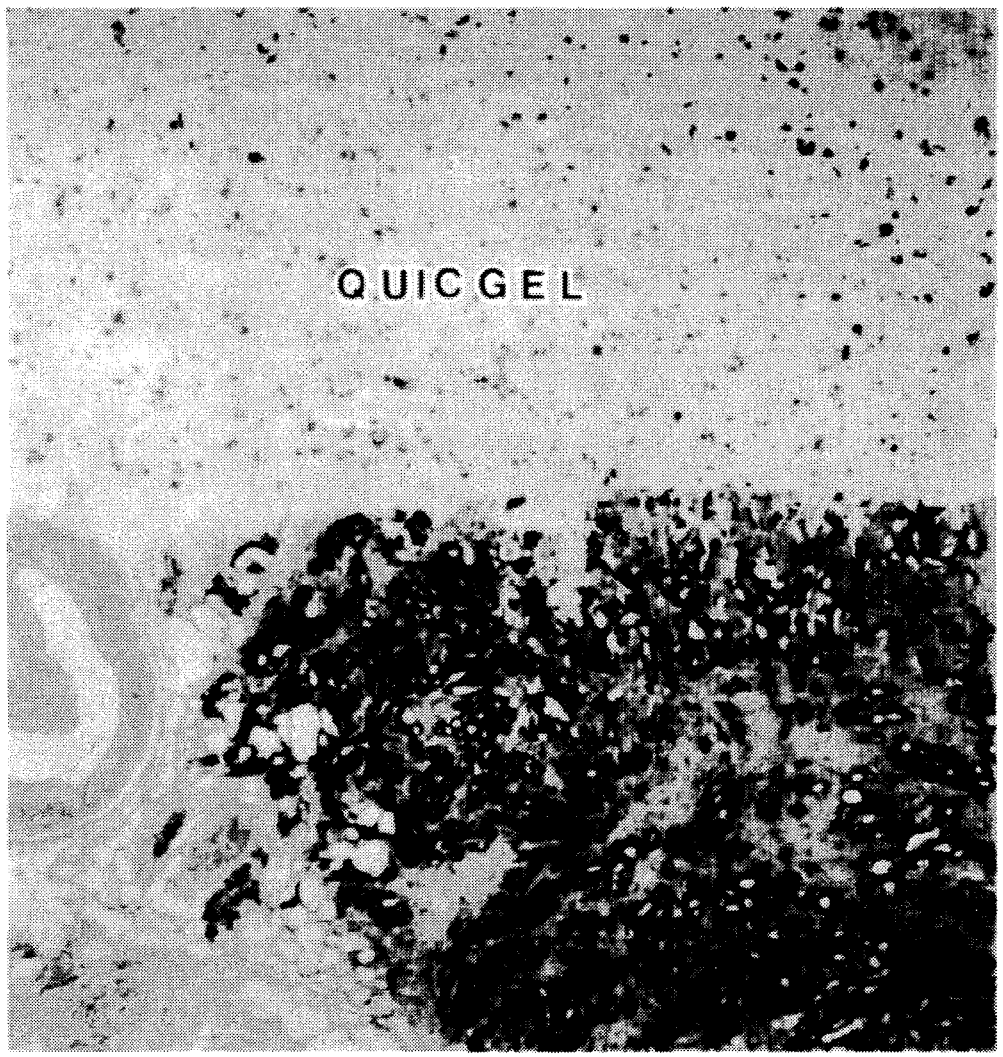
FIG. 6A is a picture of one of the gels of FIG. 6 and its corresponding breast cancer specimen shown at higher magnification. The expression "Quicgel" is a trademark owned by applicant.

Two fresh frozen samples of breast cancer, known to be estrogen receptor positive by charcoal-dextran biochemical assay were cut into portions of equivalent size and placed in tissue cassettes with a similarly sized portion of a gel prepared as that described in Example II. Four tissue cassettes were prepared for each tumor. They were fixed in NBF for 12, 24, 48, and 72 hours respectively, and processed to embedding in paraffin. To facilitate comparison, all specimens (and their respective control gels) were embedded in a single oversize paraffin block (see FIG. 6). Sections of this block were immunostained for ER as described in Example II.

A progressive reduction in the intensity of the immunoreactivity was readily detectable by conventional microscopy as the time of fixation was increased. The intensity of the immunoreactivity was similarly reduced in the corresponding gel for each sample (see FIG. 7). Measurement of the OD by CAS show that the pattern of gel and analyte are similarly affected (see FIG. 8). Note that the gradual loss of immunostaining with progressively longer fixation equally affected two different molecules being assayed (vimentin and estrogen receptor).

These results are in agreement with those of the Example II. Additionally, they confirm that the rate of antigen loss of gel and analyte as a result of the exposure to the fixative are comparable. Thus, these results support the validity of the hypothesis that the gel of the invention can be used as a standard to gauge and compensate for variations in immunoreactivity due to fixation. It is reasonable to predict that the gels will also behave in the same manner towards other causes of variation of immunoreactivity, such as temperature changes, pH of solutions and the staining procedure itself because it will be exposed to all of these variables simultaneously and equally with the analyte.

Conversion of optical density measurement to other more familiar units of measurement could be readily obtained by using appropriate formulas for each molecule being assayed.

It is important to emphasize that this same approach can be used with numerous other molecules. Estrogen receptor was used in these experiments for demonstration purposes. For other applications, gels with cells expressing suitable amounts of the molecule to be analyzed and quantitated can be similarly prepared and applied.

What is claimed is:

1. An immunocytochemical method for the direct, quantitative determination of the presence or absence of a target molecule in the cells of a tissue specimen which comprises concurrently subjecting said specimen and a control to all of the same processing steps including immunostaining, measuring the difference in optical density of said control before and after said processing steps and of said specimen after said processing steps and thereafter using said control optical density difference as a standard for determining the pre-processing optical density of said specimen, wherein said control comprises (1) a cell embedding medium; and (2) cells embedded in said medium, said embedded cells having a quantifiable level of optical density which varies with the processing steps and conditions to which said control is subjected, wherein the difference in the quantified level of optical density of said control before and after concurrent processing with the tissue specimen provides a quantitative standard for determining the pre-processing optical density of said tissue specimen.

2. A quantitative immunohistochemical method for determining the immunoreactivity of a tissue sample before processing comprising:

(i) simultaneously processing a control and said tissue sample;

(ii) determining the difference in immunoreactivity level of said control before and after processing;

(iii) determining the immunoreactivity level of said tissue sample after processing; and (iv) utilizing the difference determined in step (ii) to convert the immunoreactivity level of said tissue specimen determined in step (iii) to the pre-processing immunoreactivity level of said tissue sample wherein said control comprises (1) a cell embeddinq medium; and (2) cells embedded in said medium, said embedded cells having a quantifiable level of immunoreactivity which varies with the processing steps and conditions to which said control is subjected, wherein the difference in the quantified level of immunoreactivity of said control before and after concurrent processing with the tissue specimen provides a quantitative standard for determining the pre-processing immunoreactivity of said tissue specimen.

3. A method as defined by claim 2 wherein said immunoreactivity level determinations made in steps (iii) and (iv) include optical density measurements.

4. A method as defined by claim 2 in which said step (iv) is performed by utilizing a standard curve which is a plot of optical density against the level of immunoreactivity of said control.

5. The method of claim 1, wherein the target molecule is a cell growth factor, a receptor molecule, a molecule that controls cell proliferation or a protein expressed by an oncogene.

6. The method of claim 1, wherein the target molecule is an estrogen receptor or a progesterone receptor.

7. A method for determining the effect of preparing a tissue sample for an immunohistochemical assay on the immunoreactivity of the tissue sample comprising:

(a) preparing a cell embedded medium for an immunohistochemical assay, the embedded cells having a known level of immunoreactivity;

(b) determining the immunoreactivity of the embedded cells; and (c) determining the difference in immunoreactivity between the known level of immunoreactivity of the embedded cells prior to preparation for the immunohistochemical assay and the immunoreactivity of the embedded cells after said preparation.

8. The method of claim 7, wherein the cell embedded medium comprises agar or gelatin.

* * * * *